(12) United States Patent
Teotonio Da Silva (10) Patent No.: US 11,543,557 B2
(45) Date of Patent: Jan. 3, 2023

(54) ORGANIC CARBON CONCENTRATION USING LIBS AND AUTOCALCIMETER

(71) Applicant: Halliburton Energy Services, Inc., Houston, TX (US)

(72) Inventor: Juliana Teotonio Da Silva, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 682 days.

(21) Appl. No.: 16/528,130

(22) Filed: Jul. 31, 2019

(65) Prior Publication Data
US 2021/0032975 A1 Feb. 4, 2021

(51) Int. Cl.
| | | |
|---|---|---|
| *E21B 47/01* | (2012.01) | |
| *G01V 3/34* | (2006.01) | |
| *G01N 33/24* | (2006.01) | |
| *G01N 33/28* | (2006.01) | |
| *G01N 30/72* | (2006.01) | |

(52) U.S. Cl.
CPC ............... *G01V 3/34* (2013.01); *G01N 30/72* (2013.01); *G01N 33/24* (2013.01); *G01N 33/2835* (2013.01); *E21B 47/01* (2013.01)

(58) Field of Classification Search
CPC .......... G01V 3/34; G01N 30/72; G01N 33/24; G01N 33/2835; E21B 47/01
See application file for complete search history.

(56) References Cited

U.S. PATENT DOCUMENTS

| | | |
|---|---|---|
| 7,615,741 B2 | 11/2009 | Jacobi et al. |
| 8,618,472 B2 | 12/2013 | Suparman |
| 9,513,400 B2 | 12/2016 | Dorffer et al. |
| 9,939,361 B2 | 4/2018 | Gajji et al. |
| 10,047,604 B2 | 8/2018 | Graves et al. |
| 10,060,423 B2 | 8/2018 | Schexnaider |
| 10,144,860 B1 | 12/2018 | Reddy |
| 10,209,399 B2 | 2/2019 | Rojas et al. |
| 2012/0091328 A1* | 4/2012 | Suparman ............... G01V 5/101 250/269.1 |

FOREIGN PATENT DOCUMENTS

| | | | |
|---|---|---|---|
| EP | 3156587 A1 * | 4/2017 | ............... G01N 1/28 |
| EP | 3156587 A1 | 4/2017 | |

OTHER PUBLICATIONS

"Intact Soil Core Total, Inorganic, and Organic Carbon Measurement Using Laser-Induced Breakdown Spectroscopy" Article in Soil Science Society of America Journal, May 2011, by Bricklemyer et al (Year: 2011).*

Bernard, Bernie B., et al., "Determination of Total Carbon, Total Organic Carbon and Inorganic Carbon in Sediments," Determination of TC, TOC, and TIC in Sediments, 5 pages.

(Continued)

*Primary Examiner* — Jamil Ahmed
(74) *Attorney, Agent, or Firm* — Conley Rose, P.C.; Rodney B. Carroll (57) ABSTRACT

Disclosed herein are methods and systems that determine the carbon content of a subterranean formation by analyzing samples of drill cuttings obtained from a subterranean formation with a laser-induced breakdown spectrometer and an autocalcimeter.

20 Claims, 4 Drawing Sheets

(56) References Cited

OTHER PUBLICATIONS

Liu, Xiuju, et al., "Estimation of carbonate, total organic carbon, and biogenic silica content by FTIR and XRF techniques in lacustrine sediments," Journal of Paleolimnology, Oct. 2013, Springer Science+Business Media Dordrecht 2013.
Foreign Communication from Related Application—GCC Patent Office Examination Report, GCC Application No. GC2020-39918, dated Aug. 4, 2021, 4 pages.
Bricklemyer et al., "Intact Soil Core Total, Inorganic, and Organic Carbon Measurement Using Laser-Induced Breakdown Spectroscopy," Soil Science Society of America Journal, 2011, pp. 1006-1018, vol. 75.
Foreign Communication from Related Application - International Search Report and Written Opinion of the Internationa Searching Authority, International Application No. PCT/US2019/046531, dated Apr. 27, 2020, 11 pages.

\* cited by examiner

ORGANIC CARBON CONCENTRATION USING LIBS AND AUTOCALCIMETER

TECHNICAL FIELD

This present disclosure relates generally to the analysis of drill cuttings obtained from a subterranean formation.

BACKGROUND

Information about a subterranean formation can be obtained while drilling a wellbore by using tools to gather data relating to the subterranean formation surrounding a wellbore, referred to as "logging while drilling (LWD)." Among the various potential sources of such information are the drill cuttings from the subterranean formation. As the drill bit removes fragments of material from the bottom of the wellbore, the fragments are carried to the surface by a drilling fluid and separated from the drilling fluid. The separated material may be periodically sampled and subjected to analysis to determine desired information from the samples.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The terms "inorganic carbon concentration" and "total inorganic carbon" as used herein refer to the concentration of carbon contained in the inorganic materials that are present in a sample. For example, if a sample of drill cuttings contains calcite ($CaCO_3$), and the calcite is mostly attributable to the inorganic material present in the sample, then the sample can be considered to have an inorganic carbon concentration of 12 wt %, since stoichiometrically speaking, carbon is 12 wt % of the total weight of any amount of calcite present in the sample.

The terms "organic carbon concentration" and "total organic carbon" as used herein refer to the concentration of carbon contained in the organic materials that are present in a sample. Higher concentrations mean that a reservoir in a subterranean formation is more desirable because the concentration of carbon that is attributable to recoverable hydrocarbons is higher.

The terms "total carbon concentration," "total carbon," "total concentration of carbon" refer to the total concentration of carbon in a sample of drill cuttings and thus is the sum of the "inorganic carbon concentration" and the "organic carbon concentration" present in a sample.

The term "profile" as used herein refers to a visually presentable collection of data. For example, an "organic carbon profile" can be a spreadsheet or graphical representation of the organic carbon concentration versus the location (e.g., depth) in a subterranean formation. In another example, a "carbon profile" can be a spreadsheet or graphical representation of any combination of the total carbon concentration, inorganic carbon concentration, and organic carbon concentration versus the location (e.g., depth) in a subterranean formation.

Disclosed herein are methods and systems that determine the carbon content of a subterranean formation by analyzing samples of drill cuttings obtained from a subterranean formation with a laser-induced breakdown spectrometer and an autocalcimeter. Subterranean formations contain organic materials in the form of hydrocarbons and inorganic materials in the form of minerals like calcite and dolomite. However, the inorganic and organic materials can be intermingled with one another in a subterranean formation, and thus both materials are contained in the pieces of rock that are the drill cuttings. The ability to quantify the organic carbon concentration in a subterranean formation is valuable to understand the content of a reservoir. The utilization of the combination of the laser-induced breakdown spectrometer and autocalcimeter in the disclosed methods and systems provides a way to quantify the organic carbon concentration, along with other measurements such as total carbon and inorganic carbon concentration, and that provides improvement over commercially available techniques and improves the field of LWD.

Some commercially available analyzers that can measure the organic carbon concentration use strong acids (e.g., potassium hydrogen phthalate in combination with hydrochloric acid (HCl)) and can reach high temperatures, which raise health, safety, and environmental concerns, especially in offshore drilling environments. The disclosed methods and systems that determine the organic carbon concentration based on measurements made by a laser-induced breakdown spectrometer and an autocalcimeter provide improved techniques for determining the carbon content of a subterranean formation because the number and amount of chemicals used to determine the organic carbon concentration is reduced, and some harsh chemicals (e.g., potassium hydrogen phthalate) are not used at all. Determining the organic carbon concentration according to the disclosed methods and systems provide simpler and safer measurement of the organic carbon concentration.

Other commercially available analyzers that can measure the organic carbon concentration require very small sample sizes, for example 0.1 g per sample. In the disclosed methods and systems, the sample sizes are not as stringent, in that, the laser-induced breakdown spectrometer and the autocalcimeter can accommodate larger sample sizes (e.g., 1 g to 5 g per sample). Thus, samples are easier for a scientist or technician to prepare and analyze, especially in a drilling environment, since the amounts required for analysis (e.g., 1 g to 5 g per sample) are not so small (e.g., 0.1 g).

Moreover, determining the organic carbon concentration in accordance with the disclosed methods and systems improves the field of LWD because the data provided by the laser-induced breakdown spectrometer and autocalcimeter can be collected, stored, and presented by a surface data logging computer that already performs LWD for wellbore conditions and equipment monitoring in the drilling environment. The surface data logging computer can integrate the carbon data of the disclosed methods and system with other data received by a surface data logging computer so that the universe of data that is collected during LWD includes the total organic carbon data, total inorganic carbon data, and/or total carbon data for particular locations in the subterranean formation. An example of data integration is creating an organic carbon profile and adding organic carbon concentrations determined using the data received from the laser-induced breakdown spectrometer and autocalcimeter to the profile as the data is generated and received. Other forms of integration can include storage of carbon data for display in comprehensive reports containing spreadsheets and graphs of wellbore conditions, surface equipment status, and carbon concentrations at particular locations in the subterranean formation. Carbon data produced by the disclosed methods and systems can be integrated into LWD by the surface data logging computer to inform well-site personnel of carbon data in the subterranean formation in near-real time (e.g., the delay being lag time, the time for the drilled cutting arrive the surface, the sample preparation time and analysis time at the well-site), in addition to wellbore conditions and status of customary surface equipment (e.g., pumps, motors, etc.). Existing computer equipment for surface data logging can be used to build a carbon profile for a subterranean formation; alternatively, the computer equipment disclosed herein can be new equipment that is added to the existing surface data logging computer at a well-site in order to provide the surface data logging computer of the present disclosure.

Figure 1:
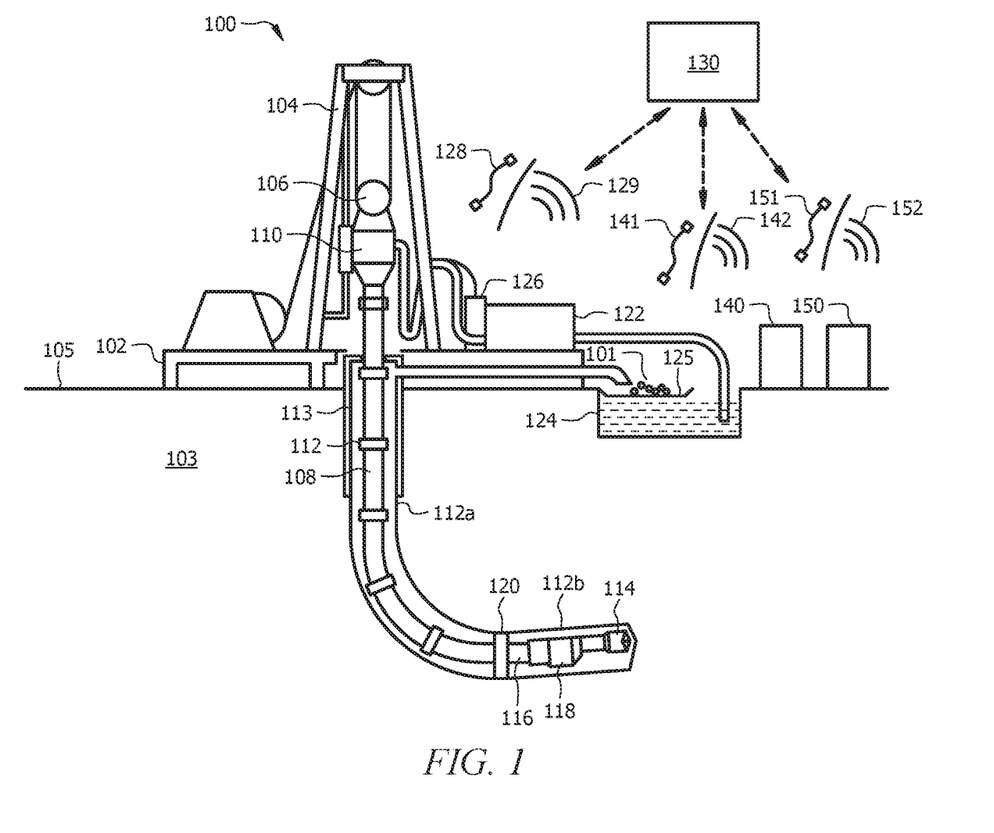
FIG. 1 is a cross-sectional view of a wellbore in a drilling environment.

FIG. 1 is a schematic view of a drilling environment 100 by which drill cuttings 101 may be obtained from a subterranean formation 103. The drilling environment 100 includes a drilling platform 102 that supports a derrick 104 having a traveling block 106 for raising and lowering a drill string 108. A top-drive motor 110 supports and turns the drill string 108 as it is lowered into a wellbore 112. The rotation of the drill string 108, alone or in combination with the operation of a downhole motor, drives the drill bit 114 to deepen or enlarge the wellbore 112.

The wellbore 112 in FIG. 1 has a vertical section 112a and a horizontal section 112b. The vertical section 112a of the wellbore 112 is vertically oriented, and the horizontal section 112b is horizontally oriented. The term "vertically oriented" as used herein may refer to a section of the wellbore 112 that has a longitudinal axis that may be exactly vertical or may extend at an angle with respect to vertical that is +/−89°, and similarly, the term "horizontally oriented" as used herein may refer to a section of the wellbore 112 that has a longitudinal axis that may be exactly horizontal or may extend at an angle with respect to horizontal that is +/−89°. Within the scope of "horizontally oriented" are those wellbore sections that are slanted and those that have a curvature, such as the curvature shown in section 112b of FIG. 1. The wellbore 112 is shown in FIG. 1 having one vertical section 112a and one horizontal section 112b; however, it is contemplated that any number of vertical and/or horizontal sections can be utilized in a wellbore. FIG. 1 illustrates that an upper portion 112a of the wellbore 112 may be stabilized with a casing string 113, and a lower portion 112b of the wellbore 112 may remain open-hole (uncased). In some embodiments, casing can be added to other portions of the wellbore 112 at any point in time, and the present disclosure is not limited to the casing configuration illustrated in FIG. 1.

A pump 122 circulates drilling fluid through a feed pipe to the top-drive motor 110, downhole through the interior of drill string 108, through orifices in the drill bit 114, back to the surface 105 via an annulus around the drill string 108, and into a fluid reservoir 124. The drilling fluid transports drill cuttings 101 from the wellbore 112 to the surface 105. Drill cuttings 101 may be extracted from the drilling fluid by any suitable technique, such as by using a shaker 125 shown in FIG. 1. In embodiments, the shaker 125 is a sieve- or basket-type device configured to allow drilling fluid to pass through holes in the shaker 125 into the reservoir 124 while drill cuttings are retained in the shaker 125.

Samples may be taken from the drill cuttings 101, cleaned, dried, and then analyzed by an autocalcimeter 150 and a laser-induced breakdown spectrometer (LIBS) 140 (discussed in detail below). Drill cuttings 101 may be a group of drill cuttings that are collected in shaker 125 for a period of time that represents an interval of depth and/or length of a newly drilled section of the wellbore 112. After the period of time elapses, samples are taken from the drill cuttings 101, and the drill cuttings 101 are removed from the shaker 125. The same process for collection and analysis of subsequent groups of drill cuttings that represent subsequent intervals of depth and/or length of newly drilled sections of the wellbore 112 is repeated, and so on, for a desired number of intervals of the wellbore 112.

In some embodiments, the autocalcimeter 150 and LIBS 140 are located at the well-site (e.g., in a surface-level laboratory or other facility containing the autocalcimeter 150 and LIBS 140), and samples may be taken from the drill cuttings 101 for analysis at the well-site. In other embodiments, samples may be taken from the drill cuttings 101 for analysis at a suitable surface-level laboratory or other facility containing the autocalcimeter 150 and LIBS 140 that is off-site.

The drill bit 114 is one component of a bottomhole assembly (BHA) 116 that may further include a rotary steering system (RSS) 118, a stabilizer 120 (or some other form of steering assembly), a navigation tool, data measurement instruments, and a control sub. The navigation tool may have instruments for measuring tool orientation (e.g., multi-component magnetometers and accelerometers). The data measurement instruments can be installed in the BHA 116 to measure downhole conditions, various drilling parameters, and characteristics of the subterranean formation 103 penetrated by the wellbore 112. The control sub coordinates the operation of the data measurement instruments, steering mechanisms, and drilling motors, in accordance with command signals received from the surface 105, and provides signals of downhole data (e.g., relevant measurement, status information) to the surface 105. Communication of data between the BHA 116 and the surface 105 may be by wireline if the drill string 108 is wired. Alternatively, the data may be communicated wirelessly using mud pulse telemetry, electromagnetic telemetry, or any other suitable wireless communication technique. In some embodiments, some or all data obtained by the control sub may be stored in memory within the BHA 116 for later retrieval, e.g., when the BHA 116 physically returns to the surface 105.

In FIG. 1, a surface communication interface 126 is configured to communicate downhole data received from the BHA 116 to a surface data logging (SDL) computer 130 and to communicate control commands to the various equipment in the wellbore 112 (e.g., the BHA 116) and on the platform 102 (e.g., pump 122, top-drive motor 110). The surface communication interface 126 may include a transmitter and a receiver suitable for wired and/or wireless communication with the BHA 116 and with the surface data logging computer 130. In some embodiments, the surface communication interface 126 has multiple transmitters and multiple receivers, wherein a first transceiver (or a transmitter/receiver pair) is configured to communicate via wired (e.g., cable) or wireless (e.g., telemetry) communication with the BHA 116 and a second transceiver (or a second transmitter/receiver pair) is configured to communicate with the surface data logging computer 130 via wired network connection 128 (e.g., Ethernet) or wireless network connection 129 (e.g., WiFi, Bluetooth®).

The surface data logging computer 130 may be embodied as: one or more embedded processors, one or more desktop computers, one or more laptop computers, one or more central processing facilities, one or more virtual computers in the cloud, or a combination thereof. In each case, software on a non-transitory information storage medium may configure the surface data logging computer 130 to carry out the desired logging, processing, modeling, and display generation. The surface data logging computer 130 is configured to communicate with the surface communication interface 126 via the wired network connection 128 (e.g., Ethernet) or the wireless network connection 129 (e.g., WiFi, Bluetooth®), collecting and processing measurement data to generate data logs and other visual representations of the acquired data and the derived models to facilitate analysis by a user.

FIG. 1 illustrates a laser-induced breakdown spectrometer (LIBS) 140 in the drilling environment 100. The LIBS 140 can be configured to communicate total carbon data to the surface data logging computer 130 via wired network connection 141 (e.g., Ethernet) and/or wireless network connection 142 (e.g., WiFi, Bluetooth®). The autocalcimeter 150 can be configured to communicate inorganic carbon data to the surface data logging computer 130 via wired network connection 151 (e.g., Ethernet) and/or wireless network connection 152 (e.g., WiFi, Bluetooth®).

The LIBS 140 is a device that is configured to determine a concentration of total carbon contained in a sample of drill cuttings 101. Carbon-containing materials are found in shale in the form of inorganic materials (as discussed above) and organic materials (e.g., hydrocarbons). The total concentration of carbon in a sample of drill cuttings 101 thus is the sum of the concentration of carbon in the inorganic materials and the concentration of carbon in the organic materials. Generally, the sample of drill cuttings 101 is pressed into a pellet for analysis by the LIBS 140. In embodiments, the sample pellet of drill cuttings 101 can have a mass from about 1 g to about 5 g; alternatively, about 2 g to about 5 g; alternatively, about 3 g to about 5 g; alternatively, about 4 g to about 5 g; alternatively, about 4 g; alternatively about 5 g; alternatively, 4 g; alternatively, 5 g. In some embodiments, the sample of drill cuttings 101 contains only solids. In some other embodiments where the same sample for the LIBS 140 was used in the autocalcimeter 150, the sample of drill cuttings 101 may contain both solids and liquid.

The LIBS 140 generally utilizes optical emission spectroscopy to measure concentration of elements in a sample of drill cuttings 101. The LIBS 140 uses a focused laser pulse to create plasma on the surface of the sample (e.g., in the form of a pellet). The creation of plasma excites material of the sample into elemental ions and atoms contained in the sample. As the plasma cools, a sensor in the LIBS 140 detects light emitted in the ultraviolet, optical, and infrared ranges of light. The LIBS 140 contains a spectrometer that is configured to analyze the wavelength and intensity of the light sensed by the LIBS 140, correlate a measured wavelength to a known wavelength for carbon, and correlate the intensity of the measured wavelength that corresponds to carbon with a concentration of the carbon in the sample. The concentration of carbon in the sample that is determined by the LIBS 140 may be used as the total concentration of carbon in the sample for the disclosed methods and systems. In additional embodiments, the LIBS 140 is configured to determine a concentration of any other element in the sample by the same steps.

The total concentration of carbon in the sample that is determined by the LIBS 140 can be stored in a local memory in the LIBS 140, stored on flash memory connected to the LIBS 140 (e.g., via a USB port or flash memory slot), sent via wired network connection 141 to the surface data logging computer 130, sent via wireless network connection 142 to the surface data logging computer 130, or a combination thereof.

In embodiments, the LIBS 140 is a handheld device that can be used at the well-site. Examples of a commercially available handheld LIBS 140 are the Z-200 and Z-300 LIBS Analyzer models available from SciAps, Inc. In embodiments of a handheld LIBS 140, the concentration of carbon and optionally other elements measured in the sample can be sent to the surface data logging computer 130 via WiFi or Bluetooth®; additionally or alternatively, the concentration data can be stored on a flash drive (e.g., via USB or other memory slot) and then uploaded to the surface data logging computer 130 via a corresponding memory slot on the surface data logging computer 130.

In embodiments, the analysis time for the LIBS 140 is within a few seconds, e.g., 1 to 2 seconds.

FIG. 1 also illustrates an autocalcimeter 150 in the drilling environment 100. The autocalcimeter 150 is a device that is configured to determine a concentration of carbon in inorganic materials contained in a sample of drill cuttings 101. Inorganic carbon-containing materials are frequently found in shale as calcium-containing minerals (e.g., calcium carbonate ($CaCO_3$, also known as calcite) and calcium magnesium carbonate ($CaMg(CO_3)_2$, also known as dolomite). A sample of drill cuttings 101 thus has calcium-containing minerals that are analyzed by the autocalcimeter 150 to determine the concentration of carbon in the inorganic materials in the sample. In embodiments, the sample of drill cuttings 101 can have a mass from about 1 g to about 5 g; alternatively, about 1 g to about 4 g; alternatively, about 1 g to about 3 g; alternatively, about 1 g to about 2 g; alternatively, about 1 g; alternatively 1 g. In additional embodiments, the sample of drill cuttings 101 can be in powder form.

The analysis by the autocalcimeter 150 can involve adding hydrochloric acid (HCl) to the sample, mixing the acid and sample together, and measuring a pressure of carbon dioxide ($CO_2$) that is evolved by the reaction of calcium-containing minerals in the sample with the HCl.

In some embodiments, the autocalcimeter 150 can be further configured to correlate the pressure of $CO_2$ to a mass of calcium-containing material in the sample, calculate the concentration of calcium-containing material in the sample by dividing the mass of calcium-containing material in the sample by the total mass of the sample, and calculate the concentration of carbon in the inorganic materials in the sample based on the concentration of calcium-containing material in the sample. In some alternative embodiments, the autocalcimeter can be further configured to correlate the pressure of $CO_2$ to directly to a mass of carbon contained in inorganic materials in the sample, and calculate the concentration of carbon in the inorganic materials in the sample by dividing the mass of carbon contained in the inorganic material in the sample by the total mass of the sample.

The mass and/or concentration of carbon in the inorganic materials of the sample can be stored in a local memory in the autocalcimeter 150, stored on flash memory connected to the autocalcimeter 150 (e.g., via a USB port or flash memory slot), sent via wired network connection 151 to the surface data logging computer 130, sent via wireless network connection 152 to the surface data logging computer 130, or a combination thereof.

In embodiments, the autocalcimeter 150 operates according to a standardized method, such as ASTM 4373-02. An example of a commercially available autocalcimeter is the Fann® AutoCalcimeter Model 442, available from the Fann Instrument Company.

In embodiments, the analysis time for the autocalcimeter 150 is about 5 minutes to about 45 minutes. For example, drill cuttings from subterranean formation that contain less than about 5% dolomite can have an analysis time of about 6 minutes in the autocalcimeter 150. Larger concentrations of dolomite in a subterranean formation can take up to about 45 minutes analysis time in the autocalcimeter 150.

The surface data logging computer 130 may be further configured to receive the total carbon concentration in the sample of drill cuttings 101 that is analyzed by the LIBS 140 and to receive the concentration of carbon contained in the inorganic materials in the sample of drill cuttings 101 that is analyzed by the autocalcimeter 150. The surface data logging computer 130 is then further configured to determine the concentration of carbon contained in the organic materials of the drill cuttings 101 using the following equation:

$$C_{organic} \text{ wt \%} = C_{total} \text{ wt \%} - C_{inorganic} \text{ wt \%}$$

where $C_{organic}$ wt % is the weight percent of carbon contained in organic materials of the sample, $C_{total}$ wt % is the weight percent of total carbon in the sample (measured by the LIBS 140), and $C_{inorganic}$ wt % is the weight percent of carbon contained in inorganic materials of the sample (measured by the autocalcimeter 150).

Alternatively, the surface data logging computer 130 may be further configured to receive the total carbon concentration in the sample of drill cuttings 101 that is analyzed by the LIBS 140 and to receive the concentration of inorganic materials contained in the sample of drill cuttings 101 that is analyzed by the autocalcimeter 150. The concentration of carbon in the inorganic materials can be calculated by the following equation, assuming calcite is the source of inorganic materials:

$$C_{inorganic} \text{ wt \%} = CaCO_3 \text{ wt \%} / 8.33$$

where $C_{inorganic}$ wt % is the weight percent of carbon contained in inorganic materials of the sample and Ca wt % is the concentration of calcite in weight percent that is received from the autocalcimeter 150. The surface data logging computer 130 is then further configured to determine the concentration of carbon contained in the organic materials of the drill cuttings 101 using the following equation:

$$C_{organic} \text{ wt \%} = C_{total} \text{ wt \%} - C_{inorganic} \text{ wt \%}$$

where $C_{organic}$ wt % is the weight percent of carbon contained in organic materials of the sample, $C_{total}$ wt % is the weight percent of total carbon in the sample (measured by the LIBS 140), and $C_{inorganic}$ wt % is the weight percent of carbon contained in inorganic materials of the sample (calculated by the surface data logging computer 130).

The disclosed methods 200, 300, 400, and 500 are illustrated in FIGS. 2 to 5. In order to perform the analysis in each of the methods 200, 300, 400, and 500, a wellbore 112 is drilled into the subterranean formation 103. Drill cuttings 101 are brought to the surface 105 via the drilling fluid and deposited in the shaker 125 for collection therefrom.

The method 200 in FIG. 2 will now be described.

Figure 2:
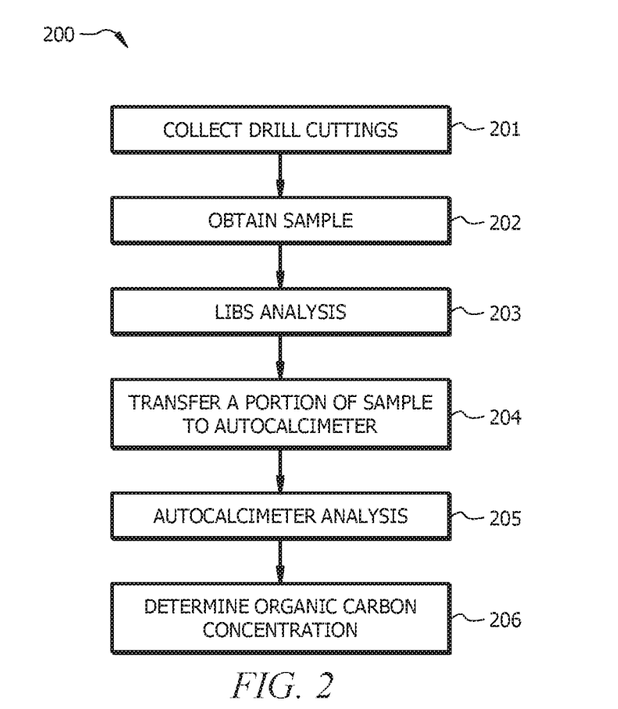
FIG. 2 is a flow diagram of a method for determining carbon content in a subterranean formation.

At step 201, the method 200 of FIG. 2 can include collecting drill cuttings from a group of drill cuttings 101, such as from the group of drill cuttings 101 in the shaker 125 of FIG. 1.

At step 202, the method 200 next includes obtaining a sample from the drill cuttings 101. Obtaining the sample can involve cleaning the collected drill cuttings, drying the cleaned drill cuttings, and forming the drill cuttings into pieces. Cleaning the drill cuttings can involve washing the drill cuttings with water and optionally with a soap to remove dirt and mud from the drill cuttings, which are pieces of the rock from the subterranean formation 103. In embodiments where soap is used to clean the drill cuttings, cleaning may include rinsing the drill cuttings with water to remove the soap residue. Drying the cleaned drill cuttings can involve allowing water on and/or in the pieces of rock to evaporate, e.g., with the aid of applied heat (e.g., in the sunlight, in an oven, heated air fan) and/or convection (e.g., a fan). Forming the drill cuttings into pieces in method 200 can include crushing or pulverizing the drill cuttings into pieces having a desired particle size that is suitable for pressing the pieces into a pellet. In some embodiments of the method 200, the drill cuttings may be crushed or pulverized such that the pieces are in powder form. A pellet is then made from the pieces of drill cuttings, wherein the sample has a mass suitable for the LIBS 140 disclosed herein (e.g., 1 g to 5 g; or 4 g to 5 g). In embodiments, the pellet can be made by pressing the pieces of drill cuttings into a mold in the shape of the pellet.

At step 203, the method 200 includes analyzing the sample with the LIBS 140 to determine a total carbon concentration in the sample. The analysis at step 203 obtains a total carbon concentration in the sample (e.g., a pellet). The total carbon concentration in the pellet is representative of the total carbon concentration in the sample of drill cuttings, which is representative of the total carbon concentration of the location (e.g., a depth, range of depths, lateral location, or a combination thereof) of the subterranean formation 103 from where the drill cuttings originated.

At step 204, the method 200 includes transferring a portion of the sample (e.g., a portion of the pellet) that was used for analysis by the LIBS 140 to the autocalcimeter 150. The portion of the sample that is transferred to the autocalcimeter 150 has a mass disclosed herein that is suitable for analysis in the autocalcimeter (e.g., 1 g to 5 g; or 1 g). In embodiments, the portion of the sample that is transferred contains only solids (e.g., the pieces of the drill cuttings). To the extent that the solids from the pellet are remain pressed together in the portion that is transferred to the autocalcimeter 150, the method 200 can include breaking up the pressed solids and if needed for solids of larger particles sizes, crushing the solids into powder form. In powder form, the solids are most suitable for analysis in the autocalcimeter 150 because the surface area for reaction is increased with smaller particle sizes.

At step 205, the method 200 includes analyzing the portion of the sample that is transferred to the autocalcimeter 150 with the autocalcimeter 150 to determine an inorganic carbon concentration or a concentration of calcium-containing material in the portion of the sample. In some embodiments, the inorganic carbon concentration is determined by the autocalcimeter 150, while in other embodiments, the inorganic carbon concentration is determined by the surface data logging computer 130. In such other embodiments where in the surface data logging computer 130 determines the inorganic carbon concentration, the surface data logging computer 130 receives a concentration of calcium-containing materials in the sample from the autocalcimeter 150 via network connection 151 or 152, or from manual user input (e.g., a keyboard, or a memory slot for a flash drive). The inorganic carbon concentration in the portion of the sample is representative of the inorganic carbon concentration in the entire sample of drill cuttings, which is representative of the inorganic carbon concentration of the location (e.g., a depth, range of depths, lateral location, or a combination thereof) of the subterranean formation 103 from where the drill cuttings originated.

At step 206, the method 200 includes determining the organic carbon concentration in the drill cuttings. As discussed above, the organic carbon concentration is determined by subtracting the inorganic carbon concentration from the total carbon concentration. The organic carbon concentration is representative of the organic carbon concentration in the entire sample of drill cuttings, which is representative of the organic carbon concentration of the location (e.g., a depth, range of depths, lateral location, or a combination thereof) of the subterranean formation 103 from where the drill cuttings originated. In some embodiments of the method 200, step 206 is performed by the surface data logging computer 130. The data for determining the organic carbon concentration can be received by any manner disclosed herein, via network connection 141 or 142, via network connection 151 or 152, or via manual user input (e.g., via a keyboard and/or memory slot for a flash drive).

In embodiments where the surface data logging computer 130 receives the concentration of calcium-containing material and not the inorganic carbon concentration, the method 200 can include determining, by the surface data logging computer 130, the inorganic carbon concentration from the concentration of calcium-containing material.

In some embodiments where the concentration of calcium-containing material is received from the autocalcimeter 150 as a concentration of calcite ($CaCO_3$) and a concentration of dolomite ($CaMg(CO_3)_2$), the concentration of calcite ($CaCO_3$) (a value received from the autocalcimeter 150) can be multiplied by 12% to determine the carbon concentration attributable to calcite in the tested sample, and the concentration of dolomite ($CaMg(CO_3)_2$) (a value received from the autocalcimeter 150) can be multiplied by 13% to determine the carbon concentration attributable to dolomite in the tested sample. The values of 12% and 13% are used because carbon is about 12 wt % of the weight of calcite ($CaCO_3$), and carbon is about 13 wt % of the weight of dolomite ($CaMg(CO_3)_2$). The inorganic carbon concentration in these embodiments is the sum of the carbon concentration attributable to calcite and the carbon concentration attributable to dolomite. The analysis time to receive the concentration of dolomite from the autocalcimeter 150 is longest, e.g., up to 45 minutes per sample.

In other embodiments where the concentration of calcium-containing material is received from the autocalcimeter 150 as a concentration of calcite ($CaCO_3$) only, the portion of the calcium-containing material that is calcite ($CaCO_3$) is the a concentration value received from the autocalcimeter 150, and the portion of the calcium-containing material that is dolomite ($CaMg(CO_3)_2$) can be approximated using the calcite concentration received from the autocalcimeter 150. For example, the autocalcimeter 150 can report the calcite concentration at 1 minute, 3 minutes, and 5 minutes analysis time (it takes longer to report dolomite concentrations, so the concentrations reported by the autocalcimeter 150 at 1, 3, and 5 minutes are calcite concentrations). The concentration of dolomite can be approximated (e.g., by the surface data logging computer 130) by subtracting the calcite concentration at 3 minutes analysis time from the calcite concentration at 5 minutes analysis time. The received concentration of calcite can be multiplied by 12% to determine the carbon concentration attributable to calcite in the tested sample, and the approximated concentration of dolomite can be multiplied by 13% to determine the approximated carbon concentration attributable to dolomite in the tested sample. The inorganic carbon concentration in these embodiments is the sum of the carbon concentration attributable to calcite and the approximated carbon concentration attributable to dolomite. An advantage of approximating the dolomite concentration is that the calcite concentration is obtained by the autocalcimeter 150 faster than is the dolomite concentration. Thus, analysis time is limited to the calcite analysis time in the autocalcimeter 150, and analyses can be performed more frequently in the autocalcimeter 150.

In some embodiments, the surface data logging computer 130 is configured to receive the total carbon concentration from the LIBS 140 via network connection 141 or 142 and the inorganic carbon concentration from the autocalcimeter 150 via network connection 151 or 152; alternatively, the surface data logging computer 130 receives the total carbon concentration and the inorganic carbon concentration from manual user input at an interface (e.g., a keyboard, or a memory slot for a flash drive) on the surface data logging computer 130; alternatively, the surface data logging computer 130 is configured to receive only one of the total carbon concentration from the LIBS 140 and the inorganic carbon concentration from the autocalcimeter 150 via network connection 141, 142, 151, or 152 and to receive the other of the total carbon concentration and the inorganic carbon concentration via manual user input.

In other embodiments, the surface data logging computer 130 is configured to receive the total carbon concentration from the LIBS 140 via network connection 141 or 142 and the concentration of calcium-containing material from the autocalcimeter 150 via network connection 151 or 152; alternatively, the surface data logging computer 130 receives the total carbon concentration and the concentration of calcium-containing material from manual user input at an interface (e.g., a keyboard, or a memory slot for a flash drive) on the surface data logging computer 130; alternatively, the surface data logging computer 130 is configured to receive only one of the total carbon concentration from the LIBS 140 and the concentration of calcium-containing material from the autocalcimeter 150 via network connection 141, 142, 151, or 152 and to receive the other of the total carbon concentration and the concentration of calcium-containing material via manual user input.

The method 300 in FIG. 3 will now be described.

Figure 3:
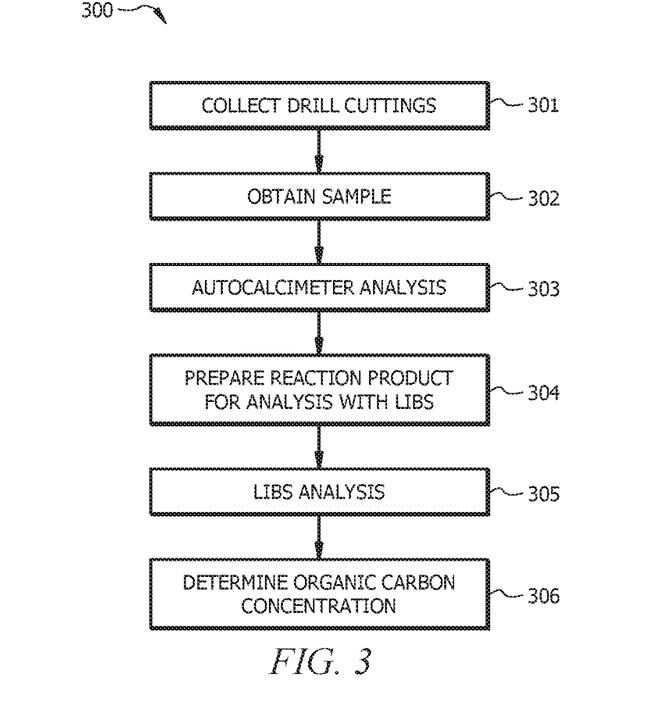
FIG. 3 is a flow diagram of an alternative method for determining carbon content in a subterranean formation.

At step 301, the method 300 of FIG. 3 can include collecting drill cuttings from a group of drill cuttings, such as from the group of drill cuttings 101 in the shaker 125 of FIG. 1.

At step 302, the method 300 next includes obtaining a sample from the drill cuttings 101. Obtaining the sample can involve cleaning the collected drill cuttings, drying the cleaned drill cuttings, and forming the drill cuttings into pieces. Cleaning and drying the drill cuttings are the same as is described for step 202 of method 200. Forming the drill cuttings into pieces in method 300 can include crushing or pulverizing the drill cuttings into a powder for use in the autocalcimeter 150. A mass of the pieces (e.g., powder) of the drill cuttings that is suitable for analysis in the autocalcimeter (e.g., 1 g to 5 g; or 1 g) is then transferred to the autocalcimeter 150. In embodiments, the sample that is placed in the autocalcimeter 150 contains only solids (e.g., the pieces or powder of the drill cuttings).

At step 303, the method 300 includes analyzing the sample with the autocalcimeter 150 to determine an inorganic carbon concentration or a concentration of calcium-containing material in the sample. In some embodiments, the inorganic carbon concentration is determined by the autocalcimeter 150, while in other embodiments, the inorganic carbon concentration is determined by the surface data logging computer 130. In such other embodiments where in the surface data logging computer 130 determines the inorganic carbon concentration, the surface data logging computer 130 receives a concentration of calcium-containing materials in the sample from the autocalcimeter 150 via network connection 151 or 152, or from manual user input (e.g., a keyboard, or a memory slot for a flash drive). The inorganic carbon concentration in the sample is representative of the inorganic carbon concentration of the location (e.g., a depth, range of depths, lateral location, or a combination thereof) of the subterranean formation 103 from where the drill cuttings originated.

At step 304, the method 300 includes preparing the reaction product from the autocalcimeter 150 for analysis in the LIBS 140. Recall that analysis in the autocalcimeter 150 involves mixing the pieces or powder of the sample of drill cuttings with HCl. HCl is a liquid at analysis conditions, thus the reaction product may contain solids and liquid. In embodiments, the reaction product may be in the form of a paste. In embodiments, to prepare the reaction product for analysis by the LIBS 140, the reaction product may be left inside the chamber of the autocalcimeter 150 and a handheld LIBS 140 may be used to analyze the reaction product while it is in the autocalcimeter chamber 150, the autocalcimeter 150 not being in operation during analysis by the LIBS 140. In alternative embodiments, preparation of the reaction product for analysis by the LIBS 140 may include removing all or a portion of the reaction product from the autocalcimeter 150 and placing the reaction product in a container or surface where a handheld LIBS 140 can focus its laser on a surface of the reaction product. In other alternative embodiments, preparation of the reaction product for analysis by the LIBS 140 may include removing all or a portion of the reaction product from the autocalcimeter 150 and placing the reaction product inside a LIBS 140 that is a stand-alone device and that is not handheld. In some embodiments, the reaction product, if in a paste, can be molded into a shape (e.g., pellet) that is suitable for analysis by the LIBS 140. The mass of the reaction product used as the sample for analysis with the LIBS 140 includes at least a portion of the mass of the solids introduced into the autocalcimeter 150.

At step 305, the method 300 includes analyzing the sample (that is the reaction product from the autocalcimeter 150) with the LIBS 140 to determine a total carbon concentration in the sample. The analysis at step 305 obtains a total carbon concentration in the sample. The total carbon concentration in the sample is representative of the total carbon concentration in the drill cuttings, which is representative of the total carbon concentration of the location (e.g., a depth, range of depths, lateral location, or a combination thereof) of the subterranean formation 103 from where the drill cuttings originated.

At step 306, the method 300 includes determining the organic carbon concentration in the drill cuttings. The determination of the organic carbon concentration is the same as described for step 206 of the method 200.

The method 400 in FIG. 4 will now be described.

At step 401, the method 400 of FIG. 3 can include collecting drill cuttings from a group of drill cuttings, such as from the group of drill cuttings 101 in the shaker 125 of FIG. 1.

Figure 4:
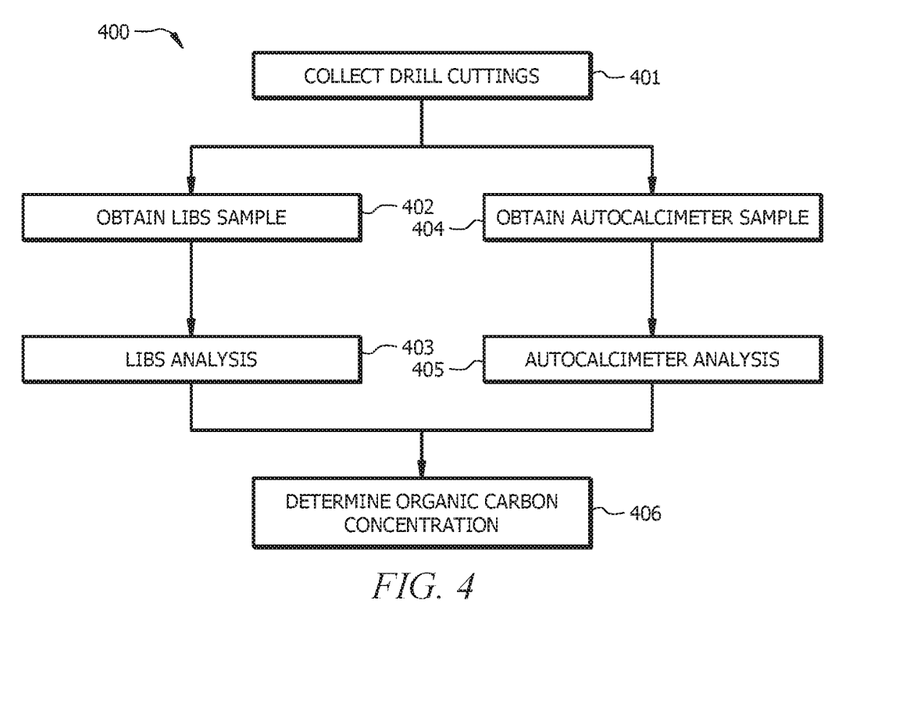
FIG. 4 is a flow diagram of an alternative method for determining carbon content in a subterranean formation.

The method 400 in FIG. 4 differs from the methods 200 and 300 of FIGS. 2 and 3 in that two samples are separately prepared for analysis by the LIBS 140 and analysis by the autocalcimeter 150 in parallel.

At step 402, the method 400 includes obtaining a sample from the drill cuttings for analysis with the LIBS 140. Obtaining the sample is the same as described in step 202 of method 200.

At step 403, the method 400 includes analyzing the sample with the LIBS 140, which is the same as described for step 203 of method 200.

At step 404, the method 400 includes obtaining a sample from the drill cuttings for analysis with the autocalcimeter 150. Obtaining the sample is the same as described in step 302 of method 300.

At step 405, the method 400 includes analyzing the sample with the autocalcimeter 150, which is the same as described for step 303 of method 300.

At step 406, the method 400 includes determining the organic carbon concentration in the drill cuttings. The determination of the organic carbon concentration is the same as described for step 206 of the method 200.

Figure 5:
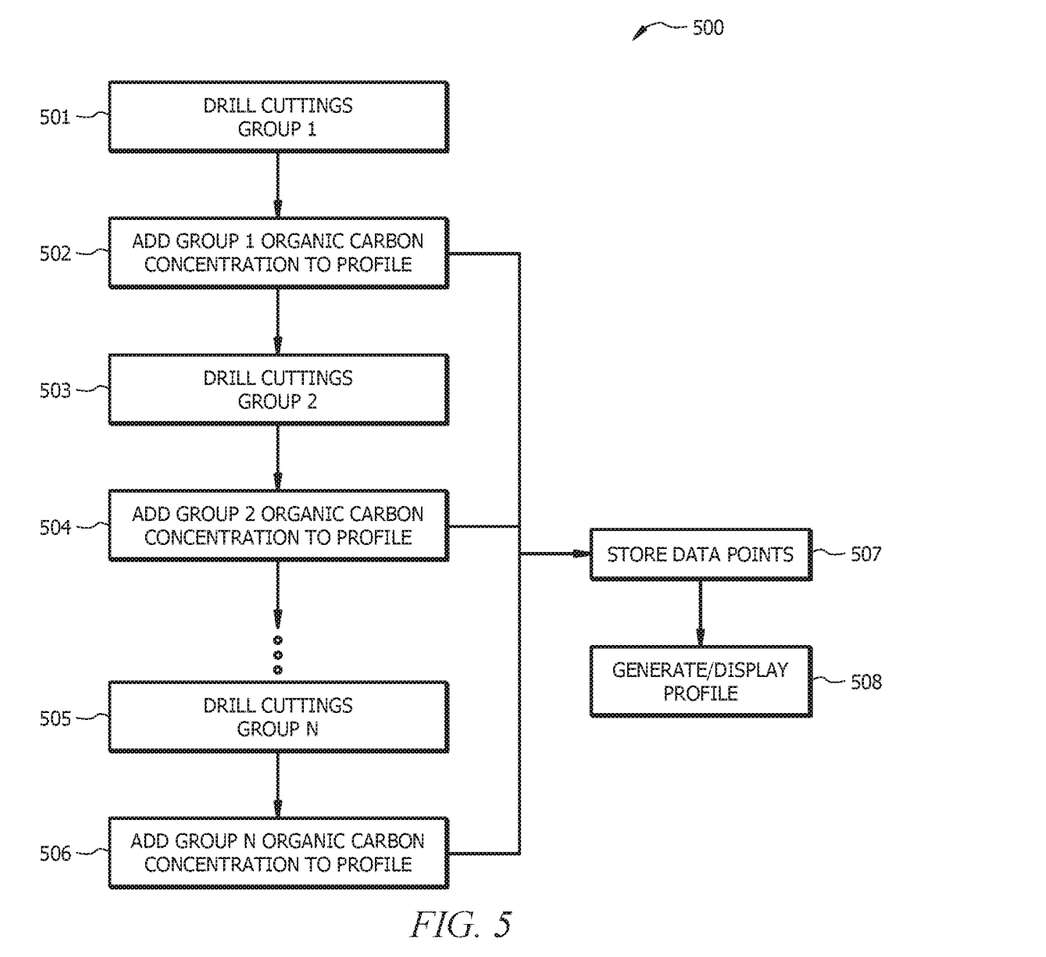
FIG. 5 is a flow diagram for building a profile for the subterranean formation that contains the carbon content determined by any of the methods shown in FIG. 2, 3, or 4.

The steps of method 500 will now be described. Generally, the steps in method 500 show how the methods 200/300/400 can be repeated for different groups of drill cuttings so as to build a profile that visually depicts the organic carbon concentration versus location in the subterranean formation 103.

At step 501, the method 500 includes performing method 200, 300, or 400 for a first group of drill cuttings that are obtained, for example, from the drilling environment 100 in FIG. 1. Performing method 200, 300, or 400 results in an organic carbon concentration for the first group of drill cuttings that is determined by the surface data logging computer 130.

At step 502, the method 500 includes adding, by the surface data logging computer 130, the organic carbon concentration corresponding to the first group of drill cuttings to an organic carbon profile for the subterranean formation 103. The surface data logging computer 130 can associate the organic carbon concentration with the location (e.g., depth, range of depths, lateral location, or a combination thereof) of the subterranean formation 103 where the first group of drill cuttings was obtained so as to produce a first organic carbon data point. Organic carbon data points can be added to the organic carbon profile, and each data point has two components: 1) the value for the organic carbon concentration and 2) the location of the subterranean formation 103.

At step 503, the method includes performing method 200, 300, or 400 for a second group of drill cuttings that are obtained, for example, from the drilling environment 100 in FIG. 1. Performing method 200, 300, or 400 results in an organic carbon concentration for the second group of drill cuttings that is determined by the surface data logging computer 130.

At step 504, the method 500 includes adding, by the surface data logging computer 130, the organic carbon concentration corresponding to the second group of drill cuttings to an organic carbon profile for the subterranean formation 103. The surface data logging computer 130 can associate the organic carbon concentration with the location (e.g., depth, range of depths, lateral location, or a combination thereof) of the subterranean formation 103 where the second group of drill cuttings was obtained so as to produce a second organic carbon data point having: 1) the value for the organic carbon concentration, and 2) the location of the subterranean formation 103.

Steps 505 and 506 indicate that the method 200, 300, or 400 can be repeatedly performed up to N groups of drill cuttings, and the organic carbon concentrations for N groups of drill cuttings can be added as N number of data points to the organic carbon profile by the surface data logging computer 130, according to the same technique described for steps 502 and 504.

Step 507 illustrates that the organic carbon concentration data points for each group of drill cuttings can be stored after said data points are obtained in steps 502, 504, and 506. The data points can be stored in a datastore of the surface data logging computer 130. Storage of the data points can be performed automatically or upon command from a user of the surface data logging computer 130.

Step 508 indicates that the surface data logging computer 130 can generate and display an organic carbon profile containing the data points. The surface data logging computer 130 can additionally generate any number of other profiles, such as inorganic carbon profile, total carbon profile, and any other profile for downhole data and/or surface data obtained by the surface data logging computer 130. Step 508 can effectively integrate the carbon data obtained according to the present disclosure with other data obtained in LWD.

ADDITIONAL DISCLOSURE

The following are non-limiting, specific embodiments in accordance with the present disclosure:

Embodiment A: A method for determining carbon content in a subterranean formation. The method includes analyzing a first sample of a first plurality of drill cuttings with a laser-induced breakdown spectrometer to determine a total carbon concentration for the first plurality of drill cuttings; analyzing a second sample of the first plurality of drill cuttings with an autocalcimeter to determine an inorganic carbon concentration for the first plurality of drill cuttings; and determining an organic carbon concentration of the first plurality of drill cuttings by subtracting the inorganic carbon concentration from the total carbon concentration.

Embodiment B, which is the method of A, wherein the first plurality of drill cuttings is representative of a first depth or of a first range of depths of the subterranean formation.

Embodiment C, which is the method of A or B, wherein analyzing a first sample is performed before analyzing a second sample.

Embodiment D, which is the method of any of A to C, wherein the second sample is a portion of the first sample obtained after analyzing the first sample.

Embodiment E, which is the method of any of A to D, wherein the portion of the first sample contains only solids.

Embodiment F, which is the method of A or B, wherein analyzing a second sample is performed before analyzing a first sample.

Embodiment G, which is the method of any of A to B and F, wherein the first sample is a portion of the second sample obtained after analyzing a second sample.

Embodiment H, which is the method of any of A to B and F to G, wherein the portion of the second sample contains solids and liquid.

Embodiment I, which is the method of any of A to H, wherein the organic carbon concentration is determined by a surface data logging computer.

Embodiment J, which is the method of I, further including adding, by the surface data logging computer, the organic carbon concentration of the first plurality of drill cuttings to an organic carbon profile for the subterranean formation.

Embodiment K, which is the method of J, wherein the organic carbon profile for the subterranean formation includes the organic carbon concentration of a second plurality of drill cuttings, wherein the second plurality of drill cuttings are representative of a second depth or of a second range of depths of the subterranean formation.

Embodiment L, which is the method of any of I to K, further including (i) receiving, by the surface data logging computer from the laser-induced breakdown spectrometer via a first network connection, the total carbon concentration; (ii) receiving, by the surface data logging computer from the autocalcimeter via a second network connection, the inorganic carbon concentration; or (iii) both (i) and (ii).

Embodiment M, which is the method of any of A to L, further including drilling a wellbore into the subterranean formation, collecting the first plurality of drill cuttings resulting from the drilling, cleaning the first plurality of drill cuttings, and obtaining the first sample, the second sample, or both from the first plurality of drill cuttings after the cleaning.

Embodiment N, which is the method of any of A to M, wherein the first sample has a mass of from about 1 g to about 5 g.

Embodiment O, which is the method of any of A to N, wherein the second sample has a mass of from about 1 g to about 5 g.

Embodiment P: A system for determining carbon content in a subterranean formation. The system can include a laser-induced breakdown spectrometer; an autocalcimeter; and a surface data logging computer networked to the laser-induced breakdown spectrometer, to the autocalcimeter, or to both the laser-induced breakdown spectrometer and the autocalcimeter.

Embodiment Q, which is the system of P, wherein the laser-induced breakdown spectrometer is configured to analyze a first sample of a first plurality of drill cuttings to determine a total carbon concentration for the first plurality of drill cuttings.

Embodiment R, which is the system of P or Q, wherein the autocalcimeter is configured to analyze a second sample of the first plurality of drill cuttings to determine an inorganic carbon concentration for the first plurality of drill cuttings.

Embodiment S, which is the system of any of P to R, wherein the surface data logging computer is configured to determine an organic carbon concentration of the first plurality of drill cuttings by subtracting the inorganic carbon concentration from the total carbon concentration.

Embodiment T, which is the system of any of P to S, wherein the first plurality of drill cuttings is representative of a first depth or of a first range of depths of the subterranean formation.

Embodiment U, which is the system of any of P to T, wherein the second sample is a portion of the first sample.

Embodiment V, which is the system of any of P to U, wherein the second sample contains only solids.

Embodiment W, which is the system of any of P to T, wherein the first sample is a portion of the second sample.

Embodiment X, which is the system of any of P to T and W, wherein the portion of the second sample contains solids and liquid.

Embodiment Y, which is the system of any of P to X, wherein the first sample has a mass of from about 1 g to about 5 g, Embodiment Z, which is the system of any of P to Y, wherein the second sample has a mass of from about 1 g to about 5 g.

Embodiment AA, which is the system of any of P to Z, wherein the surface data logging computer is further configured to add the organic carbon concentration of the first plurality of drill cuttings to an organic carbon profile for the subterranean formation.

Embodiment BB, which is the system of any of P to AA, wherein the organic carbon profile for the subterranean formation includes the organic carbon concentration of a second plurality of drill cuttings, wherein the second plurality of drill cuttings is representative of a second depth or of a second range of depths of the subterranean formation.

Embodiment CC, which is the system of any of P to BB, wherein the surface data logging computer is configured to receive, from the laser-induced breakdown spectrometer, via a first network connection, the total carbon concentration.

Embodiment DD, which is the system of any of P to CC, wherein the surface data logging computer is configured to receive, the autocalcimeter is configured to send, via a second network connection, the inorganic carbon concentration.

While embodiments have been shown and described, modifications thereof can be made by one skilled in the art without departing from the spirit and teachings of this disclosure. The embodiments described herein are exemplary only, and are not intended to be limiting. Many variations and modifications of the embodiments disclosed herein are possible and are within the scope of this disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element may be present in some embodiments and not present in other embodiments. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of this disclosure. Thus, the claims are a further description and are an addition to the embodiments of this disclosure. The discussion of a reference herein is not an admission that it is prior art, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method for determining carbon content in a subterranean formation, comprising:
    cleaning drill cuttings to remove dirt and/or mud therefrom to provide cleaned drill cuttings;
    drying the cleaned drill cutting to remove water therefrom and provide dried drill cuttings;
    analyzing a first sample of a first plurality of the dried drill cuttings with a laser-induced breakdown spectrometer (LIBS) to determine a LIBS-derived total carbon concentration for the first plurality of drill cuttings;
    analyzing a second sample of the first plurality of drill cuttings with an autocalcimeter to determine an autocalcimeter-derived inorganic carbon concentration for the first plurality of drill cuttings; and
    determining an organic carbon concentration of the first plurality of drill cuttings by subtracting the autocalcimeter-derived inorganic carbon concentration from the LIBS-derived total carbon concentration,
    wherein the first plurality of drill cuttings is representative of a first depth or of a first range of depths of the subterranean formation.

2. The method of claim 1, wherein analyzing a first sample is performed before analyzing a second sample.

3. The method of claim 2, wherein the second sample is a portion of the first sample obtained after analyzing the first sample.

4. The method of claim 3, wherein the portion of the first sample contains only solids.

5. The method of claim 1, wherein analyzing a second sample is performed before analyzing a first sample.

6. The method of claim 5, wherein the first sample is a portion of the second sample obtained after analyzing a second sample.

7. The method of claim 6, wherein the portion of the second sample contains solids and liquid.

8. The method of claim 1, wherein the organic carbon concentration is determined by a surface data logging computer, the method further comprising:
    adding, by the surface data logging computer, the organic carbon concentration of the first plurality of drill cuttings to an organic carbon profile for the subterranean formation.

9. The method of claim 8, wherein the organic carbon profile for the subterranean formation comprises the organic carbon concentration of a second plurality of drill cuttings, wherein the second plurality of drill cuttings is representative of a second depth or of a second range of depths of the subterranean formation.

10. The method of claim 8, further comprising:
(i) receiving, by the surface data logging computer from the laser-induced breakdown spectrometer via a first network connection, the LIBS-derived total carbon concentration;
(ii) receiving, by the surface data logging computer from the autocalcimeter via a second network connection, the autocalcimeter-derived inorganic carbon concentration; or
(iii) both (i) and (ii).

11. The method of claim 1, further comprising:
drilling a wellbore into the subterranean formation;
collecting the first plurality of drill cuttings resulting from the drilling;
and
obtaining the first sample, the second sample, or both from the first plurality of drill cuttings after the cleaning.

12. The method of claim 1, wherein the first sample has a mass of from about 1 g to about 5 g.

13. The method of claim 1, wherein the second sample has a mass of from about 1 g to about 5 g.

14. A system for determining carbon content in a subterranean formation, comprising:
a laser-induced breakdown spectrometer (LIBS);
an autocalcimeter; and
a surface data logging computer networked to the laser-induced breakdown spectrometer, to the autocalcimeter, or to both the laser-induced breakdown spectrometer and the autocalcimeter;
wherein:
the laser-induced breakdown spectrometer is configured to analyze a first sample of a first plurality of drill cuttings to determine a LIBS-derived total carbon concentration for the first plurality of drill cuttings;
the autocalcimeter is configured to analyze a second sample of the first plurality of drill cuttings to determine an autocalcimeter-derived inorganic carbon concentration for the first plurality of drill cuttings; and
the surface data logging computer is configured to determine an organic carbon concentration of the first plurality of drill cuttings by subtracting the autocalcimeter-derived inorganic carbon concentration from the LIBS-derived total carbon concentration,
wherein the first plurality of drill cuttings is representative of a first depth or of a first range of depths of the subterranean formation, and comprises drill cuttings that have been cleaned to remove dirt and/or mud therefrom and subsequently dried to remove water therefrom.

15. The system of claim 14, wherein the second sample is a portion of the first sample and contains only solids.

16. The system of claim 14, wherein the first sample is a portion of the second sample, and wherein the portion of the second sample contains solids and liquid.

17. The system of claim 14, wherein the first sample has a mass of from about 1 g to about 5 g, wherein the second sample has a mass of from about 1 g to about 5 g.

18. The system of claim 14, wherein the surface data logging computer is further configured to add the organic carbon concentration of the first plurality of drill cuttings to an organic carbon profile for the subterranean formation.

19. The system of claim 18, wherein the organic carbon profile for the subterranean formation comprises the organic carbon concentration of a second plurality of drill cuttings, wherein the second plurality of drill cuttings is representative of a second depth or of a second range of depths of the subterranean formation.

20. The system of claim 14, wherein:
the surface data logging computer is configured to receive, from the laser-induced breakdown spectrometer, via a first network connection, the LIBS-derived total carbon concentration; and
the surface data logging computer is configured to receive, and the autocalcimeter is configured to send, via a second network connection, the autocalcimeter-derived inorganic carbon concentration.

\* \* \* \* \*